US005888969A

United States Patent [19]

[11] Patent Number: 5,888,969
[45] Date of Patent: *Mar. 30, 1999

Girten et al.

[54] USE OF CYTOKINE RESTRAINING AGENTS TO TREAT INFLAMMATORY BOWEL DISEASE

[75] Inventors: Beverly E. Girten, San Diego; Ronald R. Tuttle, Escondido, both of Calif.

[73] Assignee: Trega Biosciences, Inc., San Diego, Calif.

[ * ] Notice: The term of this patent shall not extend beyond the expiration date of Pat. Nos. 5,420,109 and 5,726,156.

[21] Appl. No.: 911,940

[22] Filed: Jul. 14, 1997

Related U.S. Application Data

[63] Continuation of Ser. No. 336,473, Nov. 9, 1994, abandoned, which is a continuation-in-part of Ser. No. 151,534, Nov. 12, 1993, Pat. No. 5,420,109.

[51] Int. Cl.[6] .............................. A61K 38/08; C07K 7/06

[52] U.S. Cl. .............................. 514/8; 514/16; 514/17; 514/18; 514/451; 530/322; 530/329; 530/330; 549/356; 549/423; 549/424

[58] Field of Search .............................. 530/329, 330, 530/322; 514/8, 17, 18, 16, 451; 549/356, 424, 423

[56] References Cited

U.S. PATENT DOCUMENTS

| | | | |
|---|---|---|---|
| 5,114,960 | 5/1992 | Lawton et al. | 514/379 |
| 5,420,109 | 5/1995 | Suto et al. | 514/8 |
| 5,726,156 | 3/1998 | Griten et al. | 514/16 |

OTHER PUBLICATIONS

Perkins et al., "Polymer delivery of the active isomer of misoprostol: a solution to the intestinal side effect problem." *J. of Pharm. and Experimental Therapeutics,* 269 (1) :151–156 (1994).

Perkins et al., "SC–46275: A potent, long–acting gastric antisecretory prostaglandin with low oral bioavailability in the dog." *J. of Pharm. and Experimental Therapeutics,* 259 (3) :1004–1007 (1991).

Sun et al., "Effects of a polysaccharide fraction from the roots of *bupleurum falcatum* L. on experimental gastric ulcer models in rats and mice." *J. Pharm. Pharmacol.,* 43:699–704 (1991).

McCafferty et al., "Indomethacin–induced gastric injury and leukocyte adherence in arthritic versus healthy rats." *Gastroenterology,* 109:1173–1180 (1995).

Andrews et al., "Effect of nonsteroidal anti–inflammatory drugs on LFA–1 and ICAM–1 expression in gastric mucosa." *Am. J. Physiol.,* 266 (4 pt 1) :G657–64 (1994).

Santucci et al., "Role of tumor necrosis factor α release and leukocyte margination in indomethacin–induced gastric injury in rats." *Gastroenterology,* 108:393–401 (1995).

Wallace et al., "Nitric oxide–releasing non–steroidal antiinflammatory drugs: a novel approach for reducing gastorintestinal toxicity." *J. Gastroenterol Hepatol.,* 9(Suppl) 1:S40–44 (1994).

Casini–Raggi et al., "Anti–inflammatory effects of CGP 47969A, a novel inhibitor of proinflammatory cytokine synthesis, in rabbit immune colitis." *Gastroenterology,* 109:812–818 (1995).

Radford–Smith et al., "The role of cytokines in inflammatory bowel disease." *Mediators of Inflammation,* 3:3–9 (1994).

*Primary Examiner*—Cecilia J. Tsang
*Assistant Examiner*—Anish Gupta
*Attorney, Agent, or Firm*—Campbell & Flores LLP

[57] ABSTRACT

The present invention relates to the use of cytokine restraining agents to treat inflammatory bowel disease.

13 Claims, No Drawings

USE OF CYTOKINE RESTRAINING AGENTS TO TREAT INFLAMMATORY BOWEL DISEASE

This application is a continuation of U.S. application Ser. No. 08/336,473, filed Nov. 9, 1994 now abandoned, which is a continuation-in-part of U.S. application Ser. No. 08/151,534, filed Nov. 12, 1993, and issued on May 30, 1995, as U.S. Pat. No. 5,420,109, each of which applications are incorporated by reference.

BACKGROUND OF THE INVENTION

Field of the Invention

This invention relates generally to the fields of peptide chemistry and molecular pathology and, more specifically, to novel cytokine restraining agents.

Background Information

Cytokines are a class of proteins produced by macrophages and monocytes in response to viral or bacterial infection and in response to T cell stimulation during an immune response. Cytokines are normally present in very low concentrations in a tissue and mediate their effects through binding to high affinity receptors on specific cell types.

Various cytokines such as the interleukins (IL), interferons (IF) and tumor necrosis factor (TNF) are produced during immune and inflammatory responses and control various aspects of these responses. Following induction of an immune or inflammatory response, the concentrations of the various cytokines increase at different times. For example, following exposure of a subject to bacterial endotoxin, TNF and interleukin-6 (IL6) levels increase, followed a few hours later by increases in the levels of IL-1 and IL-8.

TNF, IL-1, IL-6 and IL-8 mediate host defense responses, cell regulation and cell differentiation. For example, these cytokines can induce fever in a subject, cause activation of T and B cells and affect the levels of other cytokines, which result in a cascade effect whereby other cytokines mediate the biological action of the first cytokine.

The activation of these four cytokines is responsible for the tissue damage and pain that occurs in various inflammatory conditions including, for example, rheumatoid arthritis. In rheumatoid arthritis, levels of TNF, IL-1, IL-6 and IL-8 increase dramatically and can be detected in the synovial fluid. The cytokine cascade induced by expression of these cytokines results in depressed lipoprotein metabolism as well as bone and cartilage destruction. In bacterial infections, cytokines such as IL-8 act as a signal that attracts white blood cells such as neutrophils to the region of cytokine expression. In general, the release of enzymes and superoxide anions by neutrophils is essential for destroying the infecting bacteria. However, if cytokine expression causes neutrophils to invade, for example, the lungs, release of neutrophil enzymes and superoxide anion can result in the development of adult respiratory distress syndrome, which can be lethal. Similarly, neutrophil invasion in response to cytokine expression in other tissues and organs can lead to destruction of healthy tissue.

Cytokines have multiple biological activities and interact with more than one cell type. In addition, some cells interact with more than one type of cytokine. As a result, it has not been possible to prevent damage to healthy tissue by targeting one particular cytokine or cell type. For example, individual cytokine receptors or receptor antagonists that were designed to eliminate the biological effect due to one cytokine did not decrease mortality due to endotoxic shock, which is mediated by TNF, IL-1, IL-6 and IL-8.

A better approach for preventing tissue damage due to cytokines would be to restrain the expression of all or several of the cytokines involved in the response, without eliminating expression of any cytokine in its entirety. In this way, complete immunosuppression can be prevented and homeostasis can be maintained. Corticosteroids effectively modulate cytokine expression. However, corticosteroids can cause complete immunosuppression and have other undesirable side effects such as inducing "wasting" syndrome, diabetes and osteoporosis. Non-steroidal anti-inflammatory drugs such as ketorolac (Toradol®; Syntex) also are effective in treating inflammation and pain. However, these drugs act by inhibiting prostaglandin production, which can lead to potentially severe complications including gastric ulceration, bleeding and renal failure.

In order to prevent pathological conditions caused by the expression of cytokines, it would be advantageous if cytokine levels could be readily controlled in a tissue. However, modifying the physiologic effect of cytokines has been hindered due to their pleiotropic effects. Thus, a need exists for agents that can restrain the activity of cytokines in a subject without causing undesirable side effects. The present invention satisfies this need and provides related advantages as well.

SUMMARY OF THE INVENTION

The present invention relates to novel peptides that are potent cytokine restraining agents. Novel cytokine restraining peptides having the general structures, $X_1$-$X_2$-His-(D)Phe-Arg-(D)Trp-$X_3$ and $X_4$-His-(D)Phe-Arg-(D)Trp-$X_3$, where $X_1$, $X_2$, $X_3$ and $X_4$ can be amino acids or amino acid analogs, are disclosed. The invention also relates to a cytokine restraining peptide having the structure, Ac-His-(D)Phe-Arg-(D)Trp($Ch_2$NHAc)-Gly-$NH_2$, which contains a (D)Trp analog.

In addition, the invention relates to pharmaceutical compositions comprising a pharmaceutically acceptable carrier and a cytokine restraining agent and to methods of administering the pharmaceutical composition to a subject. Administration of such a cytokine restraining agent to a subject restrains, but does not completely suppress, cytokine activity. Thus, the present invention provides a method for preventing or minimizing damage to healthy tissue caused by cytokine activity in a subject without causing complete immunosuppression in the subject.

DETAILED DESCRIPTION OF THE INVENTION

The present invention generally relates to novel cytokine restraining agents having the structure: $X_1$-$X_2$-His-(D)Phe-Arg-(D)Trp-$X_3$, wherein

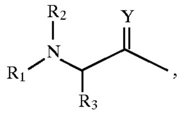, $X_1$, is

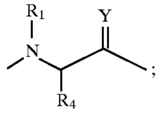

H or $COCH_3$;

$X_2$ is

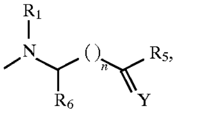

and $X_3$ is $NH_2$ or OH;

wherein Y is O, $H_2$ or S; $R_1$ is H, $COCH_3$, $C_2H_5$, $CH_2Ph$, COPh, COO-t-butyl, $COOCH_2Ph$, $CH_2CO$—(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$—$CONH_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

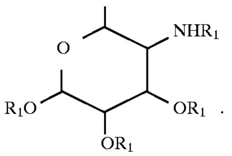

For example, the invention provides peptides such as Nle-Gln-His-(D)Phe-Arg-(D)Trp-Gly-$NH_2$; Ac-Nle-Gln-His-(D)Phe-Arg-(D)Trp-Gly-$NH_2$; and Ac-(cyclohexyl)Gly-Gln-His-(D)Phe-Arg-(D)Trp-Gly-$NH_2$, which can restrain cytokine activity.

The present invention also relates to novel cytokine restraining agents having the structure: $X_4$-His-(D)Phe-Arg-(D)Trp-$X_3$, wherein $X_4$ is

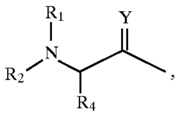

H or $COCH_3$; and $X_3$ is

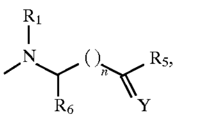

$NH_2$ or OH;

wherein Y is O, $H_2$ or S; $R_1$ is H, $COCH_3$, $C_2H_5$, $CH_2Ph$, COPh, COO-t-butyl, $COOCH_2Ph$, $CH_2CO$—(polyethylene glycol) or A; $R_2$ is H or $COCH_3$; $R_4$ is $(CH_2)_m$—$CONH_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula

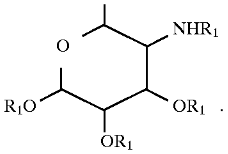

For example, the invention provides His-(D)Phe-Arg-(D)Trp-Gly-$NH_2$; Ac-His-(D)Phe-Arg-(D)Trp-$NH_2$; His-(D)Phe-Arg-(D)Trp-OH; and cyclo(His-(D)Phe-Arg-(D)Trp), which can restrain cytokine activity.

As used herein, the term "restrain" has its commonly understood meaning, i.e., to limit, restrict, keep under control or moderate. It follows that a "cytokine restraining agent" is an agent that has an action that limits or controls the biological activity of a cytokine. A cytokine restraining agent can be, for example, a peptide comprising amino acids or amino acid analogs as described herein. In addition to the examples provided above, other representative examples of peptide cytokine restraining agents include:

1) Ac—Nle—Gln—His—(D)Phe—Arg—(D)Trp—Gly—OH;
2) Ac—Nle—Gln—His—(D)Phe—Arg—(D)Trp—Gly—$OC_2H_5$;
3) Ac—Nle—Gln—His—(D)Phe—Arg—(D)Trp—Gly—NH—$NH_2$;
4) Ac—Nle—Asn—His—(D)Phe—Arg—(D)Trp—Gly—$NH_2$;
5) Ac—Nle—Asn—His—(D)Phe—Arg—(D)Trp—Gly—OH;
6) Ac—Nle—Gln—His—(D)Phe—Arg—(D)Trp—Gly—$NHCH_2CH_2Ph$;
7) Ac—Nle—Gln—His—(D)Phe—Arg—(D)Trp—Gly—$NHCH_2Ph$;
8) 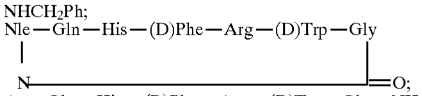
9) Ac—Gln—His—(D)Phe—Arg—(D)Trp—Gly—$NH_2$;
10) Ac—Nle—Gln—His—(D)Phe—Arg—(D)Trp—$NH_2$;
11) Ac—His—(D)Phe—Arg—(D)Trp—Gly—$NH_2$;
12) His—(D)Phe—Arg—(D)Trp—$NH_2$;
13) Ac—His—(D)Phe—Arg—(D)Trp—OH; and
14) Ac—His—(D)Phe—Arg—(D)Trp($CH_2NHAc$)—Gly—$NH_2$, where in (D)Trp($CH_2NHAc$), an analog of (D)Trp, $H_2$ replaces the α-carbonyl oxygen.

Peptide cytokine restraining agents as described above are characterized, in part, by a core structure having the amino acid sequence, His-(D)Phe-Arg-(D)Trp, or an analog of (D)Trp, where the amino acids are indicated by their commonly known three letter code and where (D) designates an amino acid having the "D" configuration, as opposed to the naturally occurring L-amino acids. Where no specific configuration is indicated, one skilled in the art would understand the amino acid to be an (L)-amino acid. In the peptides exemplified above, "Nle" is the three letter code for norleucine and "Ph" indicates a "phenyl" group ($C_6H_5$).

Cytokine restraining agents such as the peptides described above were synthesized using a modification of the solid phase peptide synthesis method of Merrifield (*J. Am. Chem. Soc.*, 85:2149 (1964), which is incorporated herein by reference) or can be synthesized using standard solution methods well known in the art (see, for example, Bodanszky, M., *Principles of Peptide Synthesis* 2nd revised ed. (Springer-Verlag, 1988 and 1993), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides were synthesized using amino acids or amino acid analogs, the active groups of which were protected as required using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

One skilled in the art would know that the choice of amino acids or amino acid analogs incorporated into the peptide will depend, in part, on the specific physical, chemical or biological characteristics required of the cytokine restraining peptide. Such characteristics are determined, in part, by the route by which the cytokine restraining agent will be administered or the location in a subject to which the cytokine restraining agent will be directed.

Selective modification of the reactive groups in a peptide also can impart desirable characteristics to a cytokine restraining agent. Peptides can be manipulated while still attached to the resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that the skilled artisan requires in the peptide.

A cyclic peptide also can be an effective cytokine restraining agent. A cyclic peptide can be obtained by inducing the formation of a covalent bond between, for example, the amino group at the N-terminus of the peptide and the carboxyl group at the C-terminus. For example, the peptide, cyclo(His-(D)Phe-Arg-(D)Trp), which can be produced by inducing the formation of a covalent bond between His and (D)Trp, can have cytokine restraining activity. Alternatively, a cyclic peptide can be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, a cyclic peptide may provide a cytokine restraining agent with increased stability in vivo.

A newly synthesized peptide can be purified using a method such as reverse phase high performance liquid chromatography (RP-HPLC), which is described in detail below (see Example I), or other methods of separation based on the size or charge of the peptide. Furthermore, the purified peptide can be characterized using these and other well known methods such as amino acid analysis and mass spectrometry, which are described in detail below (see Example I).

The invention also relates to pharmaceutical compositions comprising a cytokine restraining agent and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the cytokine restraining agent or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the cytokine restraining agent and on the particular physico-chemical characteristics of the specific cytokine restraining agent.

The invention further relates to methods of administering a pharmaceutical composition comprising a cytokine restraining agent to a subject in order to restrain pathologically elevated cytokine activity in the subject. For example, the composition can be administered to a subject as a treatment for inflammation, pain, cachexia and patho-immunogenic diseases such as arthritis, inflammatory bowel disease and systemic lupus erythematosus, each of which is characterized by pathologically elevated cytokine activity. As used herein, the term "pathologically elevated" means that a cytokine activity is elevated above a range of activities which is expected in a normal population of such subjects. For example, a normal range of IL-1 activity present in a specific tissue can be determined by sampling a number of subjects in the population. A subject having a pathology characterized by cytokine-induced pathological effects can be readily identified by determining that the cytokine activity in the subject is pathologically elevated, which is above the normal range.

One skilled in the art would know that a pharmaceutical composition comprising a cytokine restraining agent can be administered to a subject having pathologically elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. A cytokine restraining agent also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As described previously, cytokine expression can result in damage to healthy tissue in a subject and, in extreme cases, can lead to severe disability and death. Cytokines can be expressed at a site of localized infection or can be expressed systemically, for example, in an immune response or in response to bacterial endotoxin-induced sepsis. Cytokine expression can induce pyrexia (fever) and hyperalgesia (extreme sensitivity to pain) in a subject, as well as macrophage and monocyte activation, which produces or further contributes to an inflammatory response in a subject.

Since cytokine expression can be localized or systemic, one skilled in the art would select a particular route and method of administration of the cytokine restraining agent based on the source and distribution of cytokines in a subject. For example, in a subject suffering from a systemic condition such as bacterial endotoxin-induced sepsis, a pharmaceutical composition comprising a cytokine restraining agent can be administered intravenously, orally or by another method that distributes the cytokine restraining agent systemically. However, in a subject suffering from a pathology caused by localized cytokine expression such as acute respiratory distress syndrome, a cytokine restraining agent can be suspended or dissolved in the appropriate pharmaceutically acceptable carrier and administered directly into the lungs using a nasal spray.

In order to restrain the biological activity of a cytokine, the cytokine restraining agent must be administered in an effective dose, which is about 0.01 to 100 mg/kg body weight. The total ef fective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a cytokine restraining agent required to obtain an effective dose in a subject depends on many factors including the age and general health of the subject as well as the route of administration and the number of treatments to be administered. In view of these factors, the skilled artisan would adjust the particular dose so as to obtain an effective dose for restraining cytokine activity.

Examples of cytokine restraining agents and the effectiveness of a cytokine restraining agent in preventing or minimizing adverse biological effects mediated by cytokines are provided below and summarized in Tables I and II. As described below, a cytokine restraining agent such as the peptides described in Example II effectively restrain cytokine expression in mice (Examples III and IV) and provide relief from cytokine-mediated pain, swelling, fever and lethality in mice, rats and rabbits using mouse, rat and rabbit model systems that are recognized in the art as potential predictors of efficacy in humans (Examples V to XII). Thus, the compounds described herein can be used as medicaments for the treatment of pathologies such as inflammation, pain, cachexia and patho-immunogenic diseases such as arthritis, inflammatory bowel disease and systemic lupus erythematosus, which are characterized by altered cytokine activity.

The following examples are intended to illustrate but not limit the invention.

EXAMPLE I

Synthesis of a Peptide Cytokine Restraining Agents

This example describes methods for the solid phase synthesis of peptide cytokine restraining agents.

A. Nle-Gln-His-(D)Phe-Arg(D)Trp-Gly-$NH_2$

A peptide cytokine restraining agent having the amino acid sequence, Nle-Gln-His-(D)Phe-Arg-(D)Trp-Gly ("EX-1"), was synthesized using a modification of the solid phase peptide synthesis method of Merrifield (1964). Essentially, MBHA resin containing a t-BOC glycine derivative (Advanced Chemtech; Louisville, Ky.) was added to a reaction vessel suitable for solid phase peptide synthesis (see Houghten, 1985). The resin was washed three times with methylene chloride and the t-BOC protecting group was removed using trifluoroacetic acid (TFA) containing 1–2% anisole in methylene chloride. The resin then was washed with methylene chloride and treated with diisopropylethylamine.

The peptide was extended by the addition of 3.2 equivalents of N-formyl-BOC-protected D-tryptophan in dimethylformamide and 3.0 equivalents of dicyclohexylcarbodiimide. The reaction was monitored using ninhydrin and was allowed to proceed for 25 min, after which the resin was washed using methylene chloride. The procedure was repeated using di-tolulyl-BOC arginine, then with each of the desired protected amino acids until the complete heptapeptide was synthesized.

Following synthesis of the heptapeptide, the N-formyl protecting group on the tryptophan residue was removed using 20% piperidine in DMF and the resin was washed with methylene chloride. The peptide was cleaved from the resin using anhydrous hydrogen fluoride (HF) containing 10% anisole, the reaction mixture was concentrated and the residue was digested with aqueous acetic acid. The acetic acid fraction, which contained the digested sample, was removed and the residue was washed with water. The wash was added to the acetic acid fraction and the combined sample was concentrated. The resulting crude peptide was purified by RP-HPLC (Vydac, C-18 column, using a gradient of 1 to 60% solution B over 30 min (solution A is 0.1% TFA/water and solution B is 0.1% TFA/acetonitrile).

The peptide was determined to be 97% pure by RPHPLC (Vydac C-18 column, using isocratic 24% solution B; solution A and solution B. as above; absorption determined at 215 nm). The mass of the purified heptapeptide was determined by plasma absorption mass spectrometry using a BioIon 20 Mass Analyzer time of flight detector. The mass of the EX-1 peptide was measured to be 942.7, which was essentially the same as the expected molecular mass (MS (M+1)=942.2).

B. His-(D)Phe-Ara-(D)Trp($CH_2$NAc)-Gly-$NH_2$

A cytokine restraining peptide of the invention, having the amino acid sequence His-(D)Phe-Arg-(D)Trp($CH_2$NAc)-Gly-$NH_2$, was synthesized and purified as described above, except for the following modifications. Boc-(D)Trp was converted to the corresponding N,O-dimethylhydroxamate using methyl chloroformate and N,O-dimethylhydroxyl amine hydrochloride. Reduction of the tryptophan amide with lithium aluminum hydride gave the Boc-(D)Trp aldehyde.

A solution of the Boc-(D)Trp aldehyde and sodium cyanoborohydride in DMF was added to glycine attached to the rink amide resin in DMF containing 1% acetic acid. After the reductive amination was complete, the resin was shaken with 1:1 trifluoroacetic acid and methylene chloride to remove the Boc group. Sequential coupling of the remaining amino acids was performed on an peptide synthesizer (Applied Biosystems) to produce the peptide His-(D)Phe-Arg-(D)Trp($CH_2$NAc)-Gly-$NH_2$. The peptide was cleaved from the resin and purified as described above.

EXAMPLE II

Preparation of Acetylated Peptide Cytokine Restraining Agents

This example describes methods for preparing N-acetylated peptide cytokine restraining agents.

The heptapeptide Nle-Gln-His-(D)Phe-Arg-(D)Trp-Gly was synthesized as described in Example I.A., except that prior to cleaving the newly synthesized peptide from the resin, the amino terminus of the peptide was acetylated by treating the sample with acetic anhydride, diisopropylethylamine and methylene chloride for 2 hr. Following acetylation, the heptapeptide was cleaved from the resin, purified by RP-HPLC and characterized by mass spectrometry, as described above. The acetylated heptapeptide of Example II, designated, here, as EX-2, was determined to be 98% pure and the mass was measured to be 985.2 daltons, which was same as the expected molecular mass.

Similar methods as described in Examples I and II were used to synthesize other cytokine restraining peptides of the invention, including Ac-(cyclohexyl)Gly-Gln-His-(D)Phe-Arg-(D)Trp-Gly-$NH_2$ ("EX-3"); Ac-His-(D)Phe-Arg-(D)Trp-Gly-$NH_2$ ("EX-4"); and Ac-His-(D)Phe-Arg-(D)Trp-$NH_2$ ("EX-5"). Ac-His-(D)Phe-Arg-(D)Trp($CH_2$NAc)-Gly-$NH_2$ was prepared using the method described in Example I.B. except that, prior to cleaving the peptide from the resin, the peptide was acetylated using excess acetic anhydride.

EXAMPLE III

Reduction of Lipopolysaccharide-Induced Tumor Necrosis Factor Levels in Mice This example describes the effectiveness of two cytokine restraining agents for decreasing tumor necrosis factor (TNF) levels in lipopolysaccharide (LPS; endotoxin) treated mice.

Balb/c female mice weighing approximately 20 g were placed into two groups, a control group and a treated group. Five mg/kg of LPS in 0.9% saline was administered by intraperitoneal (ip) injection into the control mice. Mice in the treated group were first injected ip with 30 μg EX-2 or 150 μg EX-3 in saline, then, one minute after EX-2 or EX-3 was administered, the mice received LPS as described for the control group.

Blood samples were collected from the orbital sinus of treated and control mice at various times up to four hours after LPS was administered. The plasma was separated by centrifugation at 3000×g for 5 min, then diluted with four volumes of 1× phosphate buffer saline (pH 7.4) containing 1% bovine serum albumin. A 100 μl sample of serum was assayed by ELISA for TNF-α (Genzyme; Cambridge Mass.)

The mean (+/−SEM) TNF-α level in six mice from each group was determined and the percent reduction in TNF levels was calculated. As shown in Table I, treatment of mice with EX-2 resulted in a 50% decrease in the level of TNF-α as compared to untreated control mice. Similarly, treatment of mice with EX-3 resulted in a 56% decrease in the level of TNF-α as compared to untreated control mice (Table II). These results indicate that the peptides of the invention can restrain LPS-induced cytokine activity.

EXAMPLE IV

Reduction of Lipopolysaccharide-Induced Interleukin-6 Levels in Mice

This example describes the effectiveness of a cytokine restraining agent for decreasing interleukin-6 (IL-6) levels in LPS treated mice.

Balb/c mice were grouped and treated as described in Example III, above. Blood samples were obtained from the orbital sinus at various times up to six hours and serum was collected and diluted as described above. A 100 μl aliquot was assayed for IL-6 levels using an IL-6-specific ELISA by a modification of the method of Starnes et al., *J. Immunol.* 145:4185–4194 (1990), which is incorporated herein by reference.

The mean (+/−SEM) IL-6 level in six mice from each group was determined and the percent reduction in IL-6 was calculated. As shown in Table I, treatment of mice with EX-2 resulted in a 60% decrease in the level of IL-6 as compared to untreated control mice.

TABLE I

BIOLOGICAL DATA FOR CYTOKINE RESTRAINING AGENT, EX-2

| Biological Test | Dose | Efficacy |
|---|---|---|
| Reduction in TNF levels | 30 μg/mouse | 50% |
| Reduction in IL-6 levels | 300 μg/mouse | 60% |
| Reduction in Carageenan-induced Paw Swelling | 1 μg/mouse | 45% |
| Inhibition of LPS-induced Lethality | 11 × 300 μg/mouse | 83% |
| Recution in IL-1-induced Hyperalgesia | 1 μg/mouse | 125% |
| Reduction in LPS-induced PMN Count | 100 μg/kg | 58% |
| Reduction in IL-1-induced Fever | 500 μg/kg | 52% |
| Reduction in LPS-induced Fever | 50 μg/kg<br>150 μg/kg | 45%<br>52% |
| Reduction in arachidonic acid-induced Ear Swelling | 100 μg/mouse | 72% |
| Reduction in Morphine-induced Respiratory Depression | 10 + 20 + 20 μg/kg/rabbit | 50% |

TABLE II

BIOLOGICAL DATA FOR CYTOKINE RESTRAINING AGENT, EX-3

| Biological Test | Dose | Efficacy |
|---|---|---|
| Reduction in TNF levels | 150 μg/mouse | 56% |
| Reduction in Carageenan-induced Paw Swelling | 1 μg/mouse | 49% |
| Inhibition of LPS-induced Lethality | 11 × 300 μg/mouse | 86% |
| Reduction in LPS-induced Fever | 150 μg/kg | 57% |
| Reduction in arachidonic acid-induced Ear Swelling | 100 μg/mouse | 62% |
| Reduction in Morphine-induced Respiratory Depression | 10 + 20 + 20 μg/kg/rabbit | 65% |

EXAMPLE V

Carageenan-Induced Paw Swelling

This example describes the effectiveness of two cytokine restraining agents for alleviating inflammation and pain.

Carageenan-induced paw swelling was induced using a modification of the methods of Hiltz and Lipton, *Peptides* 11:979–982 (1990); Vinegar et al., *Fed. Proc.* 46:118–126 (1987); and Vinegar et al., *J. Pharmacol. Expt. Therap.* 166:96–103 (1969), each of which is incorporated herein by reference. Briefly, adult female Balb/c mice were anesthetized by injection of 7 mg/kg ketamine and 0.6 mg/kg rompun. Foot pad thickness was measured using a spring loaded micrometer (Swiss Precision Instruments). Foot pad thickness was expressed in units of 1/100 inch. After baseline measurements were obtained, mice were injected into a hind foot pad with either 0.2 ml physiologic saline (control) or varying doses of EX-2 or EX-3 in 0.2 ml saline (treated). The first injection was followed immediately by injection of 0.02 ml of 0.15% κ-carageenan (Sigma Chemical Co.).

Hind foot pad thickness was measured hourly for six hours, the change in thickness was determined and the percent reduction in swelling due to treatment with EX-2 was calculated. As shown in Tables I and II, ip injection of 1 μg EX-2 or 1 μg EX-3 reduced carageenan-induced swelling by 45% or 49%, respectively, when measured at the 2 hr time point.

EXAMPLE VI

Lipopolysaccharide-Induced Lethality

This example describes the effectiveness of the cytokine restraining agents, EX-2 and EX-3, in reducing lethality from sepsis induced by administration of LPS.

These experiments were performed based on information reported by Rivier et al., *Endocrinology* 125:2800–2805 (1989), which is incorporated herein by reference. Adult female Balb/c mice were provided food and water ad libitum. Mice were injected ip every four hours for 40 hr with 30 to 300 μg EX-2 or EX-3 in 0.2 ml saline (treated group) or with 0.2 ml saline, alone (control group) (10 mice per group). Immediately following the first injection, 0.6 mg LPS endotoxin in 0.2 ml saline was administered to each mouse. Following LPS injection, EX-2 or saline was administered to the treated mice or the control mice, respectively, every 4 hr for 36 hr.

As shown in Tables I and II, administration of 3.3 mg EX-2 or EX-3 (11 injections of 300 μg each) produced an 83% or 86%, respectively, increase in survival as compared to control mice. These results demonstrate that intraperitoneal administration of the cytokine restraining peptides of the invention can reduce lethality due to LPS-induced sepsis.

EXAMPLE VII

Reduction in Interleukin-1β-Induced Hyperalgesia

This example describes the effectiveness of a cytokine restraining agent, EX-2, in providing pain prophylaxis.

These experiments were performed using a modification of the methods described by Poole et al., *Br. J. Pharmacol.* 106:489–492 (1992); Follenfant et al., *Br. J. Pharmacol.* 98:41–43 (1989); and Randall and Sellito, *Arch. Internatl. Pharmacodyn.* 111:409–419 (1957), each of which is incorporated herein by reference. Adult male Sprague-Dawley rats (175–275 g) were tested for hyperalgesia by a paw pressure technique using variable pressure instrumentation (IITC Life Sciences; Woodland Hills, Calif.). Rats were acclimated to the housing environment and were handled for three days prior to beginning a training session. On the day before the hyperalgesia experiments was to begin, each rat was placed into a sock and two variable paw pressure tests were performed 15 min apart. The next day, the rats were pretested to determine the pressure (mm Hg) at which each animal exhibited escape reflexes such as whole body struggling and/or vocalization. Approximately 5–10% of the rats were non-responders and were eliminated from further experiments.

Animals that responded to the paw pressure were pretreated by ip injection of various concentrations of EX-2 in a volume of 1 ml/kg (treated) or saline, alone (control). After 20 min, 100 μl of IL-1β (1U/100 μl) was administered to rats via intraplantar injection. Two hr after IL-1 administration, rats were subjected to two additional paw pressure tests and the increase in mm Hg of pressure that could be applied to the EX-2-treated rats as compared to the control rats was determined. As shown in Table I, treatment with 1 μg EX-2 increased the amount of pressure the rats would tolerate by 125% as compared to the control rats.

EXAMPLE VIII

Adult Respiratory Distress Syndrome

This example describes the effectiveness of a cytokine restraining agent, EX-2, in minimizing respiratory distress syndrome in LPS-treated rats.

These experiments were performed using a modification of the methods described by Ulich et al., *Am. J. Pathol.* 141:61–68 (1992) and by Wheelden et al., *Lab. Animals* 26:29–37 (1992), each of which is incorporated herein by reference. Male Harlan Sprague-Dawley rats were anesthetized using a mixture of 70 mg/kg ketamine and 6 mg/kg rompun injected ip. A 2–3 cm incision was made in the neck of each anesthetized rat and its trachea was exposed by blunt dissection of the surrounding soft tissue. The rats were suspended on a near vertical slab and intratracheal injections were performed by inserting into the exposed trachea, at a point 1 cm posterior to the larynx, a 25G×½ inch needle attached to a 1 cc syringe.

Each rat received 0.5 ml/kg of saline or 0.5 ml/kg of 10 mg/ml (5 mg/kg) LPS endotoxin via slow intratracheal administration. Immediately following administration of the LPS endotoxin, rats were injected ip with 1 ml/kg of either saline (control) or saline containing various concentrations of EX-2 (treated). The rats were maintained in the elevated position for 1–2 min to facilitate distribution of the LPS and saline into the lung. The incisions were closed and the rats were allowed to recover. Two and four hr post-intratracheal injection, saline or EX-2 again was administered ip to control and treated rats, respectively.

At 6 hr post-intratracheal injection, the rats were re-anesthetized and exsanguinated via cardiac puncture. Serum was collected and saved. The neck and chest were opened to expose the trachea and lungs, the lungs were lavaged with 6×5 ml saline using a 27G×¾ inch needle and the lavage fluid was pooled.

The total polymorphonuclear leukocytes (PMN; neutrophils) in the broncho-alveolar lavage fluid were counted in the EX-2-treated rats and compared with the number in the control rats. As shown in Table I, treatment with 100 μg/kg EX-2 inhibited the increase in PMN infiltration in LPS-treated lungs by 58%.

EXAMPLE IX

Inhibition of Interleukin-1β-or Lipopolysaccharide-Induced Temperature Increase This example describes the effectiveness of the cytokine restraining agents, EX-2, EX-3and EX-4, at inhibiting body temperature increase in rats in response to two different agents.

Male Wistar rats (45–75 days old) were placed in a temperature controlled room held at 26° C., which is thermoneutral for the normal body temperature of rats, and were maintained in the room with free access to food and water for 24 hr prior to testing. On the morning of the study, rats were marked for identification and weighed. The temperature of each rat was determined by placing the animal in a restraining cage designed to minimize stress and inserting a temperature probe (YSI probe #402) 3–5 cm into the animal's rectum. The temperature was recorded 15 sec after the reading stabilized. Measurements were repeated 1 hr later to establish a baseline temperature for each rat.

After the baseline temperatures were established, rats were injected ip with saline, IL-1β or LPS endotoxin. Rats then were injected ip with either saline (control) or various concentrations of EX-2 or EX-3 (treated). The temperature of the rats was measured every hour for 6 hr and the inhibition by EX-2 or EX-3 of the rise in temperature due to IL-1β or LPS was determined.

As shown in Table I, treatment with 500 μg/kg EX-2 inhibited IL-1-induced fever by 52%. In addition, treatment with 50 or 150 μg/kg EX-2 inhibited LPS-induced fever by 45% or 52%, respectively, when measured 6 hr following LPS injection. Furthermore, treatment with 150 μg/kg EX-3 inhibited LPS-induced fever by 57% (Table II). These results demonstrate that various cytokine restraining peptides of the invention can effectively reduce fever.

EXAMPLE X

Reduction of Arachidonic Acid-Induced Ear Swelling in Mice

This example demonstrates that EX-2 and EX-3 can reduce arachidonic acid-induced ear swelling in mice.

Experiments were performed using female Balb/c mice weighing 18–23 grams. Saline or 100μg EX-2 or EX-3 was administered ip, 30 min prior to topical application of arachidonic acid (AA). A 10 μl pipet was used to apply 10 μl AA solution (100 mg/ml ethanol; Calbiochem-Novabiochem; San Diego Calif.) to the inner and outer surfaces of the right ear of each mouse. Ten μl ethanol, alone, was applied to the inner and outer surface of the left ear of each mouse.

Ear thickness was measured with a hand-held spring loaded caliper immediately before and 60 min after AA application. Increase in ear thickness was calculated by subtracting the change observed in the control ear from the change observed in AA-treated ear. The value for each group (saline and control) is the average of the swelling observed in the individual mice in each group. The percent reduction of swelling is based on the swelling observed in the saline control group. As shown in Tables I and II, EX-2 and EX-3 reduced AA-induced ear swelling by 72% and 62%, respectively.

EXAMPLE XI

Reduction of Morphine-Induced Respiration Depression in Rabbits

This example demonstrates that EX-2 and EX-3 can reduce the depression in respiration induced by morphine in rabbits.

Male Shelton rabbits (3–4 kg) were restrained and fitted around the thorax, just behind the front limbs, with a respiration transducer (Model F-RCT; Grass Instruments; Quincy Mass.). The transducer was connected to a grass polygraph via an EKG cable. An intravenous line was established for drug administration by cannulating the marginal ear vein using a 25G butterfly needle.

Rabbit breathing was allowed to stabilize, then morphine sulfate (2 mg/kg in 0.5 ml saline) was administered by intravenous (iv) injection and respiratory rate and depth were monitored for 10 min. A second dose of morphine was administered, then, after 10 min, EX-2 or EX-3 (10 μg/kg in 0.5 ml saline) was administered, iv, and rabbits were monitored for 20 min. Two additional doses of EX-2 or EX-3 (20 μg/kg in 1.0 ml saline) were administered at 20 min intervals, i.e., 40 min and 60 min after the first morphine injection.

Results were calculated as the percent change from baseline values and are expressed as the difference of the mean value of the treated group minus the mean value of the control group at the end of the experiment (80 min). As shown in Tables I and II, EX-2 and EX-3 reduced the morphine-induced respiratory depression in rabbits by 50% and 65%, respectively.

EXAMPLE XII

Effect of Orally Administered Cytokine Restraining Agents in Reducing TNF-α Levels and LPS-induced Lethality This example describes the oral effectiveness of various cytokine restraining agents in reducing LPS-induced TNF-α levels and lethality in mice.

The LPS-induced lethality studies were performed based on information reported by Rivier et al., supra, 1989. Adult female Balb/c mice were provided food and water ad libitum. Mice were administered 150 μg or 300 μg EX-2, EX-3, EX-4 or EX-5 in 100 μl saline by gavage every 4 hr for 40 hr (total doses of 1.65 mg and 3.3 mg, respectively). Control mice received 100 μl saline, alone. Immediately following the first dose of cytokine restraining agent or saline, 0.6 mg LPS in 0.2 ml saline was administered by ip injection. A statistically significant increase in survival was observed in mice receiving 3.3 mg EX-4 (63%), 1.65 mg EX-5 (68%) or 3.3 mg EX-5 (44%) as compared to control mice (0%) or mice receiving EX-2 or EX-3 (0% to 11%).

The ability of orally administered cytokine restraining agents to reduce LPS-induced TNF-α levels also was examined. Balb/c female mice (20 g) were administered 150 μg or 300 μg EX-2, EX-3, EX-4or EX-5 in 100 μl saline by gavage. Control mice received 100 μM saline, alone. One minute later, 0.1 mg LPS was administered by ip injection. Samples were collected and TNF-α levels were determined as described in Example III, above.

The mean TNF-α levels in the mice from each group (n=9–20) was determined and the percent reduction in TNF-α levels was calculated. TNF-α levels were significantly reduced in mice receiving 150 μg EX-3 (49%); 300 μg EX-3 (40%) or 300 μg EX-4 (44%) as compared to control mice (0%) and mice receiving EX-2 (26% to 28%). These results demonstrate that various cytokine restraining agents of the invention are effective when administered orally.

Although the invention has been described with areference to the examples provided above, it should be understood that various modifications can be made without departing from the spirit of the invention. Accordingly, the invention is limited only by the following claims.

We claim:

1. A method for treating inflammatory bowel disease in an individual, comprising administering to the individual an effective amount of a cytokine regulatory agent comprising $X_1$-$X_2$-His-(D)Phe-Arg-(D)Trp-$X_3$, wherein $X_1$ is

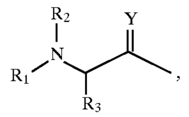

H or $COCH_3$;

$X_2$ is

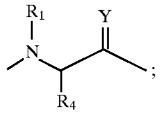

and $X_3$ is

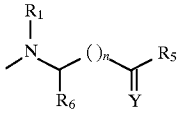

or $NH_2$;

wherein Y is O, $H_2$ or S;

$R_1$ is H, $COCH_3$, $C_2H_5$, $CH_2Ph$, COPh, $COOCH_2Ph$, COO-t-butyl, $CH_2CO$—(polyethylene glycol) or A;

$R_2$ is H or $COCH_3$;

$R_3$ is a linear or branched alkyl group having 1 to 6 carbon atoms;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula

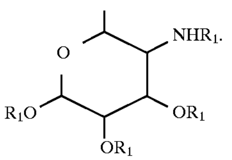

2. A method for treating inflammatory bowel disease in an individual, comprising administering to the individual an effective amount of a cytokine regulatory agent comprising $X_4$-His-(D)Phe-Arg-(D)Trp-$X_3$, wherein $X_4$ is

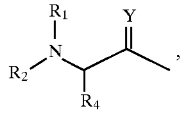

H or $COCH_3$; and $X_3$ is

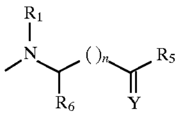

or $NH_2$;

wherein Y is O, $H_2$ or S;

$R_1$ is H, $COCH_3$, $C_2H_5$, $CH_2Ph$, COPh, $COOCH_2Ph$, COO-t-butyl, $CH_2CO$—(polyethylene glycol) or A;

$R_2$ is H or $COCH_3$;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula

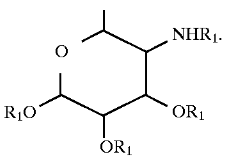

3. The method of claim 1 or 2, wherein the amino terminus is modified.

4. The method of claim 3, wherein the amino terminus is modified by acetylation.

5. The method of claim 1 or 2, wherein the carboxyl terminus is modified.

6. The method of claim 5, wherein the carboxyl terminus is modified by amidation.

7. The method of claim 1 or 2, wherein $R_1$ is selected from the group consisting of H, $C_2H_5$ and $CH_2Ph$.

8. The method of claim 1 or 2, wherein $R_1$ and $R_2$ are each H.

9. The method of claim 1, wherein $X_1$ is selected from the group consisting of norleucine, norvaline, leucine and isoleucine.

10. The method of claim 1, wherein $R_5$ is covalently bound to $X_1$, forming a cyclic peptide.

11. The method of claim 2, wherein $R_5$ is covalently bound to $X_4$, forming a cyclic peptide.

12. A method for treating inflammatory bowel disease in an individual, comprising administering to the individual an effective dose of a cytokine regulatory agent Nle-Gln-His-(D)Phe-Arg-(D)Trp-Gly-$NH_2$.

13. The method of claim 12, wherein the amino terminus is modified by acetylation.

* * * * *

UNITED STATES PATENT AND TRADEMARK OFFICE
CERTIFICATE OF CORRECTION

PATENT NO. : 5,888,969
DATED : March 30, 1999
INVENTOR(S) : Girten et al.

It is certified that error appears in the above-identified patent and that said Letters Patent is hereby corrected as shown below:

Column 2,
Line 60, insert at the start of the line -- $X_1$ is --.

Column 3,
Line 1, delete "$X_1$, is".
Line 5, insert at the start of the line -- $X_2$ is --.
Line 10, delete "$X_2$ is".
Line 15, insert at the start of the line -- $X_3$ is --.
Line 18, delete "$X_3$ is".

Column 7,
Line 32, replace "ef fective" with -- effective --.

Column 12,
Line 58, replace "EX-3and" with -- EX-3 and --.

Column 14,
Line 56, replace "arefer-" with -- refer- --.

Signed and Sealed this

Nineteenth Day of March, 2002

*Attest:*

JAMES E. ROGAN
*Director of the United States Patent and Trademark Office*

*Attesting Officer*